United States Patent [19]

Hughes

[11] Patent Number: 4,981,856
[45] Date of Patent: Jan. 1, 1991

[54] ANTI-TUMOR AGENTS

[75] Inventor: Leslie R. Hughes, Macclesfield, England

[73] Assignee: Imperial Chemical Industries PLC, London, England

[21] Appl. No.: 508,528

[22] Filed: Apr. 12, 1990

Related U.S. Application Data

[63] Continuation of Ser. No. 169,572, Mar. 17, 1988, abandoned.

[30] Foreign Application Priority Data

Mar. 25, 1987 [GB] United Kingdom ............... 8707053

[51] Int. Cl.$^5$ ............... A61K 31/505; C07D 401/12; C07D 239/90
[52] U.S. Cl. ............... 514/259; 544/284; 544/285; 544/287; 544/289
[58] Field of Search ............ 544/284, 285, 287, 289; 514/259

[56] References Cited

U.S. PATENT DOCUMENTS

| | | | |
|---|---|---|---|
| 4,447,608 | 5/1984 | Jones et al. | 544/287 |
| 4,564,616 | 1/1986 | Jones et al. | 514/260 |

FOREIGN PATENT DOCUMENTS

| | | |
|---|---|---|
| 0204529 | 12/1986 | European Pat. Off. |
| 0239362 | 9/1987 | European Pat. Off. |
| 2065653 | 7/1981 | United Kingdom |

OTHER PUBLICATIONS

Hughes, "Chemical Abstracts", vol. 108, 1988, Col. 108:205094d.
Calvert et al., Europ. J. Cancer, 16:713–722 (1980).
Jones, Europ. J. Cancer, 16:707–711 (1980).

Primary Examiner—Richard L. Raymond
Assistant Examiner—James H. Turnipseed
Attorney, Agent, or Firm—Cushman, Darby & Cushman

[57] ABSTRACT

A quinazoline of the formula:

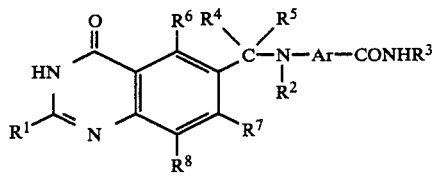

wherein $R^1$ is alkyl, cycloalkyl, alkenyl, alkynyl, alkoxy, alkylthio, aryl, aryloxy, arylthio, arylalkyl, halogeno, hydroxy or mercapto, or substituted alkyl or alkoxy;

wherein $R^2$ is hydrogen, alkyl, alkenyl or alkynyl, or substituted alkyl or alkanoyl;

wherein Ar is phenylene, naphthylene or heterocyclene which is unsubstituted or bears one or more substituents;

wherein $R^3$ is such that $R^3$—$NH_2$ is an amino acid;

wherein $R^4$ is hydrogen or alkyl;

wherein $R^5$ is hydrogen or alkyl; and wherein each of $R^6$, $R^7$ and $R^8$ is hydrogen, hydroxy, alkyl, alkoxy, alkylthio, alkylamino, dialkylamino, phenyl, halogeno, nitro, cyano or amino, or substituted alkyl, alkoxy or alkylthio;

provided that at least one of $R^4$, $R^5$, $R^6$, $R^7$ and $R^8$ is other than hydrogen;

or a pharmaceutically-acceptable salt or ester thereof. The compounds possess anti-tumour activity.

9 Claims, No Drawings

ANTI-TUMOR AGENTS

This is a continuation of application No. 07/169,572, filed Mar. 17, 1988, which was abandoned upon the filing hereof.

This invention relates to novel anti-tumour agents and more particularly it relates to quinazoline derivatives which possess anti-tumour activity.

One group of anti-tumour agents comprises the antimetabolites which are antagonists of folic acid, such as aminopterin and methotrexate. A newer compound of this type which showed considerable promise in clinical trials is known as CB3717 and is described and claimed in United Kingdom Patent Specification No. 2065653B. Despite its promise, however, CB3717 shows symptoms of toxicity in humans, particularly in relation to the liver and kidney.

Compounds of this type are believed to act as antitumour agents by inhibiting the enzyme thymidylate synthetase. Their anti-tumour activity may be assessed in vitro by determining their inhibitory effect on that enzyme, and in cell cultures by their inhibitory effect on the cell line L1210.

We have now found that certain quinazoline derivatives are considerably more active than CB3717, and furthermore are more water-soluble than that compound, which may be clinically important by increasing the ease of clearance through the kidney thereby decreasing any symptoms of toxicity.

According to the invention there is provided a quinazoline of the formula:

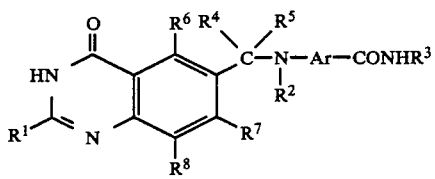

wherein $R^1$ is alkyl, cycloalkyl, alkenyl, alkynyl, alkoxy or alkylthio each of up to 6 carbon atoms;

or $R^1$ is aryl, aryloxy, arylthio or arylalkyl each of up to 10 carbon atoms;

or $R^1$ is halogeno, hydroxy or mercapto;

or $R^1$ is alkyl of up to 3 carbon atoms which bears one or more substituents selected from halogeno, hydroxy, amino, alkoxy, alkanoyloxy, alkylthio, alkylamino, dialkylamino and alkanoylamino each of up to 6 carbon atoms and arylthio, aroyloxy and aroylamino each of up to 10 carbon atoms;

or $R^1$ is alkoxy of up to 3 carbon atoms which bears one or more substituents selected from hydroxy and alkoxy of up to 6 carbon atoms;

wherein $R^2$ is hydrogen, alkyl, alkenyl, alkynyl, hydroxyalkyl, alkoxyalkyl, mercaptoalkyl, alkylthioalkyl, halogenoalkyl, cyanoalkyl, aminoalkyl, alkylaminoalkyl, dialkylaminoalkyl, alkanoylalkyl, carboxyalkyl, carbamoylalkyl or alkanoyl each of up to 6 carbon atoms or aroylalkyl of up to 10 carbon atoms;

wherein Ar is phenylene, naphthylene or heterocyclene which is unsubstituted or which bears one or more substituents selected from halogeno, phenyl, cyano, nitro, hydroxy, amino and carbamoyl and alkyl, alkoxy, halogenoalkyl, alkanoylamino, alkylthio and alkoxycarbonyl each of up to 6 carbon atoms;

wherein $R^3$ is such that $R^3-NH_2$ is an amino acid;

wherein $R^5$ is hydrogen or alkyl, of up to 4 carbon atoms; and wherein each of $R^6$, $R^7$ and $R^8$ is hydrogen, hydroxy, alkyl, alkoxy, alkylthio, alkylamino or dialkylamino each of up to 4 carbon atoms; or is phenyl, halogeno, nitro, cyano or amino; or is alkyl, alkoxy or alkylthio each of up to 4 carbon atoms which bears one or more substituents selected from halogeno, hydroxy, amino, alkoxy, alkylamino and dialkylamino each of up to 4 carbon atoms; provided that at least one of $R^4$, $R^5$, $R^6$, $R^7$ and $R^8$ is other than hydrogen;

or a pharmaceutically-acceptable salt or ester thereof.

It will be observed that a quinazoline of the invention may possess one or more asymmetric carbon atoms and it can therefore exist in racemic and optically active forms. It is to be understood that this invention encompasses a racemic form of the quinazoline and any optically-active form thereof which possesses anti-tumour activity, it being a matter of common general knowledge how a racemic compound may be separated into its optically-active forms.

A suitable value for $R^1$, $R^2$, $R^4$, $R^5$, $R^6$, $R^7$ or $R^8$ when it is alkyl, or for an alkyl substituent in Ar is, for example, methyl, ethyl, propyl, isopropyl or tert-butyl.

A suitable value for $R^1$ when it is cycloalkyl is, for example, cyclopropyl, cyclopentyl or cyclohexyl.

A suitable value for $R^1$ or $R^2$ when it is alkynyl is, for example, prop-2-ynyl, but-2-ynyl, but-3-ynyl, pent-2-ynyl, 3-methylpent-4-ynyl, hex-2-ynyl or hex-5-ynyl.

A suitable value for $R^1$, $R^6$, $R^7$ or $R^8$ when it is alkoxy or alkylthio, or for an alkoxy or alkylthio substituent in Ar is, for example, methoxy, ethoxy, isopropoxy, tert-butoxy, methylthio or isopropylthio.

A suitable value for $R^1$ when it is aryl or arylalkyl is, for example, phenyl, tolyl, benzyl, α-methylbenzyl or phenethyl.

A suitable value for $R^1$ when it is aryloxy or arylthio is, for example, phenoxy, tolyloxy, phenylthio or tolylthio.

A suitable value for $R^1$, $R^6$, $R^7$ or $R^8$ when it is halogeno is, for example, fluoro, chloro, bromo or iodo.

A suitable value for $R^1$ when it is substituted alkyl is, for example, fluoromethyl, difluoromethyl, trifluoromethyl, 2-fluoroethyl, 3-fluoropropyl, chloromethyl, dichloromethyl, hydroxymethyl, 2hydroxyethyl, 3-hydroxypropyl, aminomethyl, 3-aminopropyl, methoxymethyl, isopropoxymethyl, 3-methoxypropyl, acetoxymethyl, propionyloxymethyl, methylthiomethyl, 3-methylthiopropyl, propylthiomethyl, methylaminomethyl, propylaminomethyl, methylaminopropyl, dimethylaminomethyl, diethylaminomethyl, ethylmethylaminomethyl, 3-dimethylaminopropyl, acetamidomethyl, 3-acetamidopropyl, propionamidomethyl, phenylthiomethyl, tolylthiomethyl, benzoyloxymethyl or benzamidomethyl.

A suitable value for $R^1$ when it is substituted alkoxy is, for example, 2-hydroxyethoxy, 4-hydroxybutoxy, 3-hydroxy-2-methylpropoxy, 2-methoxyethoxy, 3-methoxypropoxy or 2-ethoxyethoxy.

A suitable value for $R^2$ when it is hydroxyalkyl, alkoxyalkyl, mercaptoalkyl or alkylthioalkyl is, for example, 2-hydroxyethyl, 3-hydroxypropyl, 2-methoxyethyl, 2-ethoxyethyl, 3-methoxypropyl, 2- methoxypropyl, 2-mercaptoethyl, 3-mercaptopropyl, 2-methythioethyl, 3-methylthiopropyl or 2-ethylthioethyl.

A suitable value for $R^2$ when it is halogenoalkyl, cyanoalkyl, aminoalkyl, alkylaminoalkyl or dialkylaminoalkyl is, for example, 2-fluoroethyl, 2-chloroethyl, 2-bromoethyl, 3-fluoropropyl, 3-chloropropyl, cyanomethyl, 2-cyanoethyl, 3-cyanopropyl, 2-aminoethyl, 3-aminopropyl, 3-amino-2-methylpropyl, 2-methylaminoethyl, 2-dimethylaminoethyl, 2-ethylaminoethyl, 2-diethylaminoethyl, 3-methylaminopropyl or 3-dimethylaminopropyl.

A suitable value for $R^2$ when it is alkanoylalkyl, carboxyalkyl, carbamoylalkyl or alkanoyl is, for example, acetonyl, 2-acetylethyl, propionylmethyl, 2-propionylethyl, 3-acetylpropyl, 4-acetylbutyl, carboxymethyl, 2-carboxyethyl, carbamoylmethyl, acetyl, propionyl or butyryl.

A suitable value for $R^2$ when it is aroylalkyl is, for example, phenacyl or 2-benzoylethyl.

A suitable value for Ar when it is heterocyclene is, for example, a 5-membered or 6-membered aromatic (that is, fully unsaturated) heterocyclene diradical which contains up to 2 heteroatoms selected from the group consisting of oxygen, nitrogen and sulphur, for example, thienylene, pyridylene, pyrimidinylene, thiazolylene or oxazolylene.

A suitable halogeno, halogenoalkyl, alkanoylamino or alkoxycarbonyl substituent in Ar is, for example, fluoro, chloro, bromo, iodo, fluoromethyl, difluoromethyl, trifluoromethyl, acetamido, propionamido, isopropionamido, methoxycarbonyl, ethoxycarbonyl or isobutoxycarbonyl.

A suitable value for $R^3$ is such that $R^3$-$NH_2$ is a naturally-occurring amino acid such as L-aspartic acid, L-glutamic acid, L-alanine, L-phenylalanine, L-serine, glycine, L-ornithine, L-valine, L-leucine or L-isoleucine. Alternatively $R^3$ may be such that $R^3$-$NH_2$ is L-2-aminobutyric acid or a poly-L-glutamic acid of the formula:

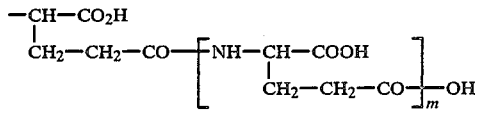

wherein m is an integer from 1 to 10.

Alternatively $R^3$ may be such that $R^3$-$NH_2$ is L-norvaline, L-alloisoleucine, L-2-phenylglycine or L-tert-leucine.

For the avoidance of doubt it is stated that:
L-ornithine is L-2,5-diaminopentanoic acid;
L-norvaline is L-2-aminopentanoic acid;
L-2-phenylglycine is (2S)-α-aminophenylacetic acid; and
L-tert-leucine is L-2-amino-3,3-dimethylbutyric acid.

The structures of the other amino acids are well known to those skilled in the art but for the purposes of reference the reader is directed to *Pure and Applied Chemistry*, 1974, 40, 317 and *European Journal of Biochemistry*, 1984, 138, 9.

A suitable value for $R^6$, $R^7$ or $R^8$ when it is alkylamino or dialkylamino is, for example, methylamino, isopropylamino, dimethylamino, ethylmethylamino or diethylamino.

A suitable value for $R^6$, $R^7$ or $R^8$ when it is substituted alkyl, substituted alkoxy or substituted alkylthio is, for example, fluoromethyl, difluoromethyl, trifluoromethyl, 2-fluoroethyl, 3-fluoropropyl, chloromethyl, dichloromethyl, hydroxymethyl, 2-hydroxyethyl, 3-hydroxypropyl, aminomethyl, 3-aminopropyl, methoxymethyl, isopropoxymethyl, 3-methoxypropyl, methylaminomethyl, propylaminomethyl, methylaminopropyl, dimethylaminomethyl, diethylaminomethyl, ethylmethylaminomethyl, 3-dimethylaminopropyl, 1-fluoro-1-methylethyl, 1-chloro-1-methylethyl, 1-hydroxy-1-methylethyl, 1-methoxy-1-methylethyl, 1-amino-1-methylethyl, 1-methylamino-1-methylethyl, 1-dimethylamino-1-methylethyl, 2-fluoroethoxy, 2-hydroxyethoxy, 2-aminoethoxy, 2-methoxyethoxy, 2-methylaminoethoxy, 2-dimethylaminoethoxy, 2-fluoroethylthio, 2-hydroxyethylthio, 2-aminoethylthio, 2-methoxyethylthio, 2-methylaminoethylthio or 2-dimethylaminoethylthio.

A suitable pharmaceutically-acceptable salt of a quinazoline of the invention is, for example, an acid addition salt with, for example, an inorganic or organic acid, for example hydrochloric, hydrobromic, trifluoroacetic or maleic acid; or an alkali metal, for example sodium, alkaline earth metal, for example calcium, or ammonium, for example tetra(2-hydroxyethyl)ammonium, salt.

A suitable pharmaceutically-acceptable ester of a quinazoline of the invention is, for example, an ester with an aliphatic alcohol of up to 6 carbon atoms, for example a methyl, ethyl or tert-butyl ester.

It is to be understood that when $R^3$ contains two carboxylic acid residues, that is, when it is derived from, for example, aspartic or glutamic acid, a salt or ester may be a mono-acid-mono-salt or ester or it may be a di-salt or ester.

A particular quinazoline of the invention has the formula stated above wherein $R^1$ is alkyl (especially methyl, ethyl and isopropyl), cycloalkyl (especially cyclopropyl), alkenyl (especially prop-2-enyl), alkynyl (especially prop-2-ynyl), alkoxy (especially methoxy and ethoxy) or alkylthio (especially methylthio) each of up to 6 carbon atoms; or $R^1$ is aryl (especially phenyl and tolyl), aryloxy (especially phenoxy) or arylalkyl (especially benzyl and phenethyl) each of up to 10 carbon atoms; or $R^1$ is halogeno (especially chloro and bromo), hydroxy or mercapto; or $R^1$ is alkyl of up to 3 carbon atoms which bears one or more (especially one, two and three) substituents selected from halogeno, hydroxy, amino, alkoxy, alkanoyloxy, alkylthio, alkylamino, dialkylamino and alkanoylamino each of up to 6 carbon atoms (especially fluoromethyl, difluoromethyl, trifluoromethyl, 2-fluoroethyl, chloromethyl, hydroxymethyl, 2-hydroxyethyl, aminomethyl, methoxymethyl, acetoxymethyl, methylthiomethyl, methylaminomethyl, dimethylaminomethyl and acetamidomethyl); or $R^1$ is alkoxy of up to 3 carbon atoms which bears one or more (especially one and two) substituents selected from hydroxy and alkoxy of up to 6 carbon atoms (especially 2-hydroxyethoxy, 2-methoxyethoxy and 2-ethoxyethoxy); wherein $R^2$ is hydrogen, alkyl (especially methyl, ethyl and propyl), alkenyl (especially prop-2-enyl and but-2-enyl), alkynyl (especially prop-2-ynyl and but-2-ynyl), hydroxyalkyl (especially 2-hydroxyethyl and 3-hydroxypropyl), alkoxyalkyl (especially 2-methoxyethyl and 3-methoxypropyl), mercaptoalkyl (especially 2-mercaptoethyl), alkylthioalkyl (especially 2-methylthioethyl), halogenoalkyl (especially 2-fluoroethyl, 2-chloroethyl, 2-bromoethyl and 3-fluoropropyl), cyanoalkyl (especially cyanomethyl and 2-cyanoethyl), aminoalkyl methylaminoethyl), dialkylaminoalkyl (especially 2-dimethylaminoethyl), alkanoylalkyl (especially acetonyl), carboxyalkyl (especially carboxymethyl), carbamoylalkyl (especially carbamoylmethyl) or alkanoyl (especially acetyl)

each of up to 6 carbon atoms; wherein Ar is phenylene (especially 1,4-phenylene) or heterocyclene (especially thienylene, pyridylene, pyrimidinylene, thiazolylene and oxazolylene) which is unsubstituted or which bears one or more (especially one and two) substituents selected from halogeno (especially fluoro, chloro and bromo), phenyl, cyano, nitro, hydroxy, amino and carbamoyl and alkyl (especially methyl and ethyl), alkoxy (especially methoxy and ethoxy), halogenoalkyl (especially fluoromethyl, difluoromethyl and trifluoromethyl) and alkanoylamino (especially acetamido) each of up to 6 carbon atoms;

wherein $R^3$ is such that $R^3$-$NH_2$ is an amino acid (especially L-glutamic acid, L-aspartic acid, L-alanine, L-phenylalanine, L-serine, glycine, L-ornithine, L-valine, L-leucine, L-isoleucine, L-2-aminobutyric acid, L-norvaline, L-alloisoleucine, L-2-phenylglycine and L-tert-leucine);

wherein $R^4$ is hydrogen or alkyl (especially methyl and ethyl), of up to 4 carbon atoms;

wherein $R^5$ is hydrogen or alkyl (especially methyl and ethyl), of up to 4 carbon atoms; and wherein each of $R^6$, $R^7$ and $R^8$ is hydrogen, hydroxy, alkyl (especially methyl and ethyl), alkoxy (especially methoxy and ethoxy), alkylthio (especially methylthio), alkylamino (especially methylamino) or dialkylamino (especially dimethylamino) each of up to 4 carbon atoms; or is phenyl, halogeno (especially fluoro, chloro and bromo), nitro, cyano or amino; or is alkyl of up to 4 carbon atoms which bears one or more (especially one, two and three) substituents selected from halogeno and hydroxy (especially fluoromethyl, difluoromethyl, trifluoromethyl, 2-fluoroethyl, hydroxymethyl and 2-hydroxyethyl); provided that at least one of $R^4$ $R^5$, $R^6$, $R^7$ and $R^8$ is other than hydrogen;

or a pharmaceutically-acceptable salt or ester thereof.

A preferred quinazoline of the invention has the formula stated above wherein $R^1$ is methyl, ethyl, isopropyl, cyclopropyl, prop-2-enyl, prop-2-ynyl, methoxy, ethoxy, methylthio, phenyl, tolyl, phenoxy, benzyl, phenethyl, chloro, bromo, hydroxy, mercapto, fluoromethyl, difluoromethyl, trifluoromethyl, 2-fluoroethyl, chloromethyl, hydroxymethyl, 2-hydroxyethyl, aminomethyl, methoxymethyl, acetoxymethyl, methylthiomethyl, methylaminomethyl, dimethylaminomethyl, acetamidomethyl, 2-hydroxyethoxy, 2-methoxyethoxy or 2-ethoxyethoxy;

wherein $R^2$ is hydrogen, methyl, ethyl, propyl, prop-2-enyl, but-2-enyl, prop-2-ynyl, but-2-ynyl, 2-hydroxyethyl, 3-hydroxypropyl, 2-methoxyethyl, 3-methoxypropyl, 2-mercaptoethyl, 2-methylthioethyl, 2-fluoroethyl, 2-chloroethyl, 2-bromoethyl, 3-fluoropropyl, cyanomethyl, 2-cyanoethyl, 2-aminoethyl, 2-methylaminoethyl, 2-dimethylaminoethyl, acetonyl, carboxymethyl, carbamoylmethyl or acetyl;

wherein Ar is 1,4-phenylene, thienylene, pyridylene, pyrimidinylene, thiazolylene or oxazolylene which is unsubstituted or which bears one or two substituents selected from fluoro, chloro, bromo, phenyl, cyano, nitro, hydroxy, amino, carbamoyl, methyl, ethyl, methoxy, ethoxy, fluoromethyl, difluoromethyl, trifluoromethyl and acetamido;

wherein $R^3$ is such that $R^3$-$NH_2$ is L-glutamic acid, glycine, L-alanine, L-phenylalanine, L-serine, L-ornithine, L-aspartic acid; L-valine, L-leucine, L-isoleucine, L-2-aminobutyric acid, L-norvaline, L-alloisoleucine, L-2-phenylglycine or L-tert-leucine;

wherein $R^4$ is hydrogen, methyl or ethyl wherein $R^5$ is hydrogen, methyl or ethyl and wherein each of $R^6$, $R^7$ and $R^8$ is hydrogen, hydroxy, methyl, ethyl, methoxy, ethoxy, methylthio, methylamino, dimethylamino, phenyl, fluoro, chloro, bromo, nitro, cyano, amino, fluoromethyl, difluoromethyl, trifluoromethyl, 2-fluoroethyl, hydroxymethyl or 2-hydroxyethyl; provided that at least one of $R^4$, $R^5$, $R^6$, $R^7$ and $R^8$ is other than hydrogen;

or a pharmaceutically-acceptable salt or ester thereof.

An especially preferred quinazoline of the invention has the formula stated above wherein $R^1$ is methyl, ethyl, methoxy, fluoromethyl or hydroxymethyl;

wherein $R^2$ is hydrogen, methyl, ethyl, prop-2-enyl, prop-2-ynyl, 2-hydroxyethyl, 3-hydroxypropyl, 2-fluoroethyl, 2-bromoethyl, cyanomethyl or acetonyl;

wherein Ar is 1,4-phenylene, thien-2,5-diyl, pyrid-2,5-diyl or thiazol-2,5-diyl which is unsubstituted or which bears one or two substituents selected from fluoro, chloro, hydroxy, amino and methyl;

wherein $R^3$ is such that $R^3$-$NH_2$ is L-glutamic acid, L-valine, L-leucine, L-isoleucine, L-2-aminobutyric acid, L-norvaline, L-alloisoleucine, L-2-phenylglycine or L-tert-leucine;

wherein $R^4$ is hydrogen or methyl;

wherein $R^5$ is hydrogen;

wherein $R^6$ is hydrogen, methyl, methoxy, fluoro or chloro;

wherein $R^7$ is hydrogen, methyl, methoxy, fluoro or chloro and wherein $R^8$ is hydrogen, methyl, methoxy, fluoro or chloro; provided that at least one of $R^4$, $R^6$, $R^7$ and $R^8$ is other than hydrogen.

In each of the cases wherein Ar is pyrid-2,5-diyl or thiazol-2,5-diyl it will be observed that two isomeric quinazolines of the invention are possible with the group —$CONHR^3$ in either the 2- or 5-position. It is to be understood that this invention encompasses any of these isomeric forms which possess anti-tumour activity.

A further especially preferred quinazoline of the invention has the formula stated above wherein $R^1$ is methyl, ethyl, methoxy, fluoromethyl or hydroxymethyl;

wherein $R^2$ is hydrogen, methyl, ethyl, prop-2-enyl, prop-2-ynyl, 2-hydroxyethyl, 3-hydroxypropyl, 2-fluoroethyl or acetonyl;

wherein Ar is 1,4-phenylene, thien-2,5-diyl, pyrid-2,5-diyl or 2- fluoro-1,4-phenylene;

wherein $R^3$ is such that $R^3$-$NH_2$ is L-glutamic acid;

wherein $R^4$ is hydrogen or methyl;

wherein $R^5$ is hydrogen;

wherein $R^6$ is hydrogen or chloro;

wherein $R^7$ is hydrogen, methyl, fluoro or chloro and wherein $R^8$ is hydrogen, methoxy or chloro; provided that at least one of $R^4$, $R^6$, $R^7$ and $R^8$ is other than hydrogen.

A further especially preferred quinazoline of the invention has the formula stated above wherein $R^1$ is methyl;

wherein $R^2$ is hydrogen, methyl, ethyl, prop-2-ynyl or 2-fluoroethyl;

wherein Ar is 1,4-phenylene or thien-2,5-diyl; or is pyrid-2,5-diyl or thiazol-2,5-diyl each with the group -$CONHR^3$ in the 2-position; or is 2-fluoro-1,4-phenylene with the group -$CONHR^3$ in the 1-position;

wherein $R^3$ is such that $R^3$-$NH_2$ is L-glutamic acid, L-valine, L-2-phenylglycine or L-tert-leucine;

wherein $R^4$ is hydrogen or methyl;

wherein $R^5$ is hydrogen;

wherein $R^6$ is hydrogen or chloro;

wherein $R^7$ is hydrogen, methyl, methoxy, fluoro or chloro and wherein $R^8$ is hydrogen, methyl, methoxy or chloro; provided that at least one of $R^4$, $R^6$, $R^7$ and $R^8$ is other than hydrogen.

Specific particularly preferred quinazolines of the invention form the group of compounds:

N-[p-[N-(3,4-dihydro-2,7-dimethyl-4-oxoquinazolin-6-ylmethyl)-N-(prop-2-ynyl)amino]benzoyl]-L-glutamic acid, N-[p-[N-(3,4-dihydro-2,7-dimethyl-4-oxoquinazolin-6-ylmethyl)-N-methylamino]benzoyl]-L-glutamic acid, N-[p-[N-(7-fluoro-3,4-dihydro-2-methyl-4-oxoquinazolin-6-ylmethyl)-N- (prop-2-ynyl)amino]benzoyl]-L-glutamic acid, N-[p-[N-(7-chloro-3,4-dihydro-2-methyl-4-oxoquinazolin-6-ylmethyl)-N-(prop-2-ynyl)amino]benzoyl]-L-glutamic acid, N-[p-[N-(3,4-dihydro-8-methoxy-2-methyl-4-oxoquinazolin-6-ylmethyl)-N-(prop-2-ynyl)amino]benzoyl]-L-glutamic acid, N-[p-N-[1-(3,4-dihydro-2-methyl-4-oxoquinazolin-6-yl)ethyl]-N-(prop-2ynyl)amino]benzoyl]-L-glutamic acid and N-[p-[N-[1-(3,4-dihydro-2-methyl-4-oxoquinazolin-6-yl)ethyl]-N-methylamino]benzoyl]-L-glutamic acid.

Further specific particularly preferred quinazolines of the invention form the group of compounds:

N-[4-[N-(3,4-dihydro-2,7-dimethyl-4-oxoquinazolin-6-ylmethyl)-N-(propynyl)amino]-2-fluorobenzoyl]-L-glutamic acid, N-[5-[N-(3,4-dihydro-2,7-dimethyl-4-oxoquinazolin-6-ylmethyl)-N-ethylaminol]-2-thenoyl]-L-glutamic acid, N-[5-[N-(3,4-dihydro-2,7-dimethyl-4-oxoquinazolin-6-ylmethyl)-N-methylamino]picolinoyl]-L-glutamic acid.

N-[5-[N--(3,4-dihydro-2,7-dimethyl-4-oxoquinazolin-6-ylmethyl)-N-methylamino]thiazole-2-carbonyl]-L-glutamic acid, N-[p[N-(3,4-dihydro-2,7-dimethyl-4-oxoquinazolin-6-ylmethyl)-N-(prop-2-ynyl)amino]benzoyl]-L-valine and N-4-[N-(3,4-dihydro-2,7-dimethyl-4-oxoquinazolin-6-ylmethyl)-N-(prop-2-ynyl)amino]-2-fluorobenzoyl]-L-valine.

A quinazoline of the invention may be prepared by any process known to be applicable to the preparation of chemically-related compounds.

A preferred process for the manufacture of a quinazoline of the invention comprises the reaction of a compound of the formula:

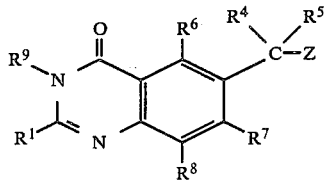

with a compound of the formula:

and within these compounds $R^1$, $R^2$, $R^3$, $R^4$, $R^5$, $R^6$, $R^7$, $R^8$ and Ar have the meanings stated above, provided that when there is a hydroxy group in $R^1$, $R^3$, $R^6$, $R^7$, $R^8$ or Ar, when there is a hydroxalkyl group in $R^1$, $R^2$, $R^6$, $R^7$ or $R^8$, when there is a hydroxyalkoxy group in $R^1$, $R^6$, $R^7$ or $R^8$, when there is a hydroxyalkylthio group in $R^6$, $R^7$ or $R^8$, when there is an amino group in $R^3$, $R^6$, $R^7$, $R^8$ or Ar, when there is an aminoalkyl group in $R^1$, $R^2$, $R^6$, $R^7$ or $R^8$, when there is an alkylaminoalkyl group in $R^1 R^2 R^6 R^7$ or $R^8$, when there is an alkylamino, alkylaminoalkoxy, alkylaminoalkylthio, aminoalkoxy or aminoalkylthio group in $R^6$, $R^7$ or $R^8$, when there is a carboxy or carboxyalkyl group in $R^2$ or $R^3$ or when there is a mercapto or mercaptoalkyl group in $R^1$, $R^2$ or $R^3$ any amino, carboxy and mercapto group is protected by a conventional protecting group and any hydroxy group may be protected by a conventional projecting group or alternatively any hydroxy group need not be protected;

$R^9$ is hydrogen or a protecting group and Z is a displaceable group; whereafter any undesired protecting group in $R^1$, $R^2$, $R^3$, $R^6$, $R^7$, $R^8$ and Ar or any protecting group $R^9$ is removed by conventional means.

A suitable protecting group for a hydroxy group is, for example, an esterifying group, for example an acetyl or benzoyl group, which may be removed by hydrolysis with a base, for example sodium hydroxide, or provided that $R^1$ and $R^2$ do not contain an alkenyl or alkynyl group, the protecting group may be, for example, an α-arylalkyl group, for example a benzyl group, which may be removed by hydrogenation over a catalyst, for example palladium-on-charcoal.

A suitable protecting group for an amino group may be, for example, an alkoxycarbonyl group, for example a tert-butyloxycarbonyl group which may be removed by treatment with an organic acid, for example trifluoroacetic acid; or it may be, for example, a benzyloxycarbonyl group which may be removed by treatment with a Lewis acid, for example boron tris(trifluoroacetate).

A suitable alternative protecting group for a primary amino group is, for example, a phthaloyl group which may be removed by treatment with an alkylamine, for example dimethylaminopropylamine or with hydrazine.

A suitable protecting group for a carboxy group may be an esterifying group, for example a methyl or an ethyl group which may be removed by hydrolysis with a base, for example sodium hydroxide; or, for example a tert-butyl group which may be removed by treatment with an organic acid, for example trifluoroacetic acid.

A suitable protecting group for a mercapto group is, for example, an esterifying group, for example an acetyl group, which may be removed by hydrolysis with a base, for example sodium hydroxide.

A suitable value for $R^9$ when it is a protecting group is, for example, a pivaloyloxymethyl group which may be removed by hydrolysis with a base, for example sodium hydroxide Z may be, for example, a halogeno or sulphonyloxy group, for example a chloro, bromo, methanesulphonyloxy or toluene-p-sulphonyloxy group.

The protecting groups for the various carboxy groups in $R^3$ may be esterifying groups such as permit the product after removal of any undesired protecting groups in $R^1$, $R^2$, $R^3$, $R^6$, $R^7$, $R^8$ and Ar and of any protecting group $R^9$ to fall within the definition of a quinazoline of the invention. In such instance the carboxy protecting groups in $R^3$ may be removed or they may be retained. Alternatively a different protecting group may be used which will be removed.

A further preferred process for the manufacture of a quinazoline of the invention comprises the reaction of an acid of the formula:

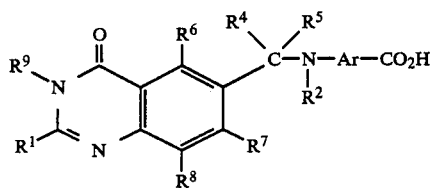

or a reactive derivative thereof, with a compound of the formula $R^3$-$NH_2$, wherein $R^1$, $R^2$, $R^3$, $R^4$, $R^5$, $R^6$, $R^7$, $R^8$, $R^9$ and Ar have the meanings stated above and any mercapto, amino, alkylamino and carboxy group in $R^1$, $R^2$, $R^3$, $R^6$, $R^7$, $R^8$ and Ar is protected by a conventional protecting group, as stated above, and any hydroxy group in $R^1$, $R^2$, $R^3$, $R^6$, $R^7$, $R^8$ and Ar may be protected by a conventional protecting group, as stated above or alternatively any hydroxy group need not be protected; whereafter the protecting groups are removed by conventional means.

A suitable reactive derivative of an acid of the formula given above may be, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an acyl azide, for example an azide formed by the reaction of the acid and an azide such as diphenylphosphoryl azide; or the product of the reaction of the acid and a carbodiimide, for example dicyclohexylcarbodiimide.

The carboxylic acid used as starting material may be obtained by the reaction of a compound of the formula:

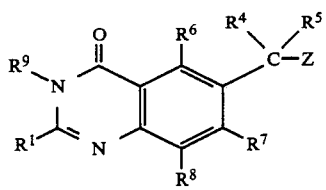

wherein $R^1$, $R^4$, $R^5$, $R^6$, $R^7$, $R^8$, $R^9$ and Z have the meanings stated above, with a compound of the formula:

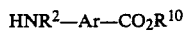

HNR$^2$—Ar—CO$_2$R$^{10}$ wherein $R^2$ and Ar have the meanings stated above and $R^{10}$ is a protecting group which can be removed to provide a carboxylic acid.

$R^{10}$ may be, for example, a methyl or an ethyl group which may be removed by hydrolysis with a base, for example sodium hydroxide or $R^{10}$ may be, for example, a tert-butyl group which may be removed by cleavage with an organic acid, for example trifluoroacetic acid.

The protecting group for the carboxy group in $R^{10}$ may be, for example, an esterifying group which can be removed while the protecting group for any mercapto, amino, carboxy and hydroxy group in $R^1$, $R^2$, $R^6$, $R^7$, $R^8$ and Ar is retained.

A further preferred process for the manufacture of a quinazoline of the invention, wherein $R^1$ is alkoxy, aryloxy or alkoxy of up to 3 carbon atoms which bears one or more substituents selected from hydroxy and alkoxy, comprises the reaction of a compound of the formula:

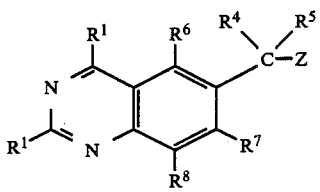

with a compound of the formula:

HNR$^2$—Ar—CONHR$^3$ wherein $R^1$ has the last-mentioned meaning stated above;

wherein $R^2$, $R^3$, $R^4$, $R^5$, $R^6$, $R^7$, $R^8$ and Ar have the meanings stated above, provided that any mercapto, amino, alkylamino and carboxy group in $R^2$, $R^3$, $R^6$, $R^7$, $R^8$ and Ar is protected by a conventional protecting group, as stated above, and any hydroxy group in $R^1$, $R^2$, $R^3$, $R^6$, $R^7$, $R^8$ and Ar may be protected by a conventional protecting group, as stated above or alternatively any hydroxy group need not be protected;

whereafter the protecting groups are removed by conventional means as stated above and the $R^1$ group situated at the 4-position of the quinazoline ring is cleaved by hydrolysis with a base, for example sodium hydroxide, to form a quinazoline of the invention.

A further preferred process for the manufacture of a quinazoline of the invention, wherein $R^1$ is mercapto, alkylthio arylthio, alkylthioalkyl or arylthioalkyl comprises the reaction of a quinazoline of the formula:

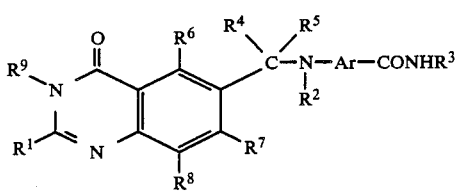

wherein $R^1$ is halogeno or halogenoalkyl and $R^2$, $R^3$, $R^4$, $R^5$, $R^6$, $R^7$, $R^8$, $R^9$ and Ar have the meanings stated above, provided that any mercapto, amino, alkylamino, carboxy and hydroxy group in $R^2$, $R^3$, $R^6$, $R^7$, $R^8$ and Ar may be protected by a conventional protecting group, as stated above or alternatively any amino, alkylamino, carboxy and hydroxy group need not be protected; with thiourea to provide a compound wherein $R^1$ is mercapto; or with an alkyl or aryl thiol to provide a compound wherein $R^1$ is alkylthio, arylthio, alkylthioalkyl or arylthioalkyl whereafter the protecting groups are removed by conventional means, as stated above.

A further preferred process for the manufacture of a quinazoline of the invention wherein $R^1$ is alkylthio comprises the reaction of a quinazoline of the formula:

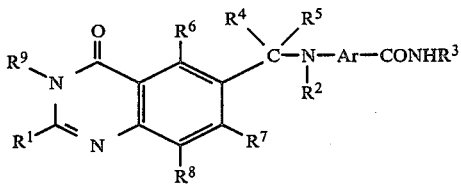

wherein $R^1$ is mercapto and $R^2$, $R^3$, $R^4$, $R^5$, $R^6$, $R^7$, $R^8$, $R^9$ and Ar have the meanings stated above, provided that any mercapto, amino, alkylamino, carboxy and hydroxy group in $R^2$, $R^3$, $R^6$, $R^7$, $R^8$ and Ar may be protected by a conventional protecting group, as stated above or alternatively any amino, alkylamino, carboxyl and hydroxy group need not be protected; with a base, for example ammonium hydroxide, followed by alkylation of the resultant thiolate salt with an alkyl halide, for example methyl iodide; whereafter the protecting groups, if present, are removed by conventional means, as stated above.

As stated above a quinazoline of the invention possesses anti-tumour activity and may itself be active thus or it may be a prodrug which is converted in vivo to an active compound. As also stated above a quinazoline of the invention is believed to act as an anti-tumour agent by inhibiting the enzyme thymidylate synthetase. This anti-tumour activity may be assessed in vitro by determining the inhibitory effect on that enzyme and is cell cultures by the inhibitory effect on the mouse leukaemia cell line L1210 (UK Patent Specification No. 2065653B).

Although the pharmacological properties of quinazolinas of the invention vary with structural change, in general quinazolines of the invention possess thymidylate synthetase inhibitory properties at the following concentrations: $IC_{50}$ in the range, for example, 0.01–10 $\mu M$; or quinazolines of the invention possess L1210 cell-line inhibitory properties at the following concentrations: $IC_{50}$ in the range, for example, 0.01–50 $\mu M$.

In general those quinazolines of the invention which are especially preferred possess thymidylate synthetase inhibitory properties at the following concentrations: $IC_{50}$ in the range, for example, 0.01–1 $\mu M$; or they possess L1210 cell-line inhibitory properties at the following concentrations: $IC_{50}$ in the range, for example, 0.01–5 $\mu M$.

Thus, by way of example, the quinazoline, N-[p-[N-(3,4-dihydro-2,7-dimethyl-4-oxoquinazolin-6-ylmethyl)-N-(prop-2ynyl)amino]benzoyl]-L-glutamic acid has an $IC_{50}$ of 0.03 $\mu M$ against thymidylate synthetase and an $IC_{50}$ of 0.18 $\mu M$ against the L1210 cell line.

A quinazoline of the invention may be administered to a warm-blooded animal, including a human, in the form of a pharmaceutical composition which comprises the quinazoline in association with a pharmaceutically-acceptable diluent or carrier.

The composition may be in a form suitable for oral administration, as a tablet or capsule, or, especially, for parenteral injection, as a sterile solution, suspension or emulsion, or for topical administration, as an ointment or cream, of for rectal administration as a suppository.

The composition may contain, in addition to the quinazoline of the invention, one or more other anti-tumour substances selected from, for example, mitotic inhibitors, for example vinblastine; alkylating agents, for example cis-platin, carboplatin and cyclophosphamide; other antimetabolites, for example 5-fluorouracil, cytosine arabinoside and hydroxyurea; intercalating antibiotics, for example adriamycin and bleomycin; enzymes, for example asparaginase; topoisomerase inhibitors, for example etoposide and biological response modifiers, for example interferon.

The quinazoline will normally be administered to a warm-blooded animal at a dose within the range 50–5000 mg per square meter body area of the animal.

The invention is illustrated but not limited by the following Examples:

The structures of all compounds of the invention were confirmed by proton magnetic resonance and mass spectroscopy and by elemental analysis. Proton magnetic resonance spectra were determined using a Jeol FX 90Q or a Bruker AM200 spectrometer operating at a field strength of 200 MHz. Chemical shifts are reported in parts per million downfield from tetramethylsilane as an internal standard (6 scale) and peak multiplicities are shown thus; s, singlet; d, doublet; d of d's, doublet of doublets; t, triplet; m, multiplet. Fast-atom bombardment (FAB) mass spectral data were obtained using a VG Analytical MS9 spectrometer and xenon gas and, where appropriate, either positive ion data oz negative ion data were collected.

Column chromatography was performed using Merck Art 9385 silica gel.

EXAMPLE 1

A mixture of 6-bromomethyl-3,4-dihydro-2,7-dimethylquinazolin-4-one (1.07 g), diethyl N-[p-(prop-2-ynyl)aminobenzoyl]-L-glutamate (UK Patent Specification No. 2065653B; 1.44 g), 2,6-lutidine (1.4 ml) and dimethylformamide (8 ml) was stirred at 80° C. under an atmosphere of argon for 24 hours. The mixture was cooled to laboratory temperature, a mixture of ice and water (10 ml) was added and the resultant mixture was stirred for 2 hours and filtered. The solid obtained was dried and purified by chromatography on a silica gel column using ethyl acetate as eluent.

A mixture of the product thus obtained (0.4 g), ethanol (3.5 ml) and aqueous N-sodium hydroxide solution (2.2 ml) was stirred at laboratory temperature for 20 hours. The mixture was evaporated to dryness, the residue was dissolved in de-ionised water and the solution was acidified to pH 2.5 by adding aqueous 2N-hydrochloric acid solution. The mixture was centrifuged and the solid residue was washed with water (4×20 ml) and dried. There was thus obtained N-[p-[N-(3,4-dihydro-2,7-dimethyl-4-oxoquinazolin-6-ylmethyl)-N-(prop-2-ynyl)amino]benzoyl]-L-glutamic acid (containing 1.5 equivalents of water; 0.2 g), m.p. 182° C. (decomposes).

NMR Spectrum: (CD$_3$SOCD$_3$) 2.0 (m, 2H, CH$_2$), 2.35 (broad t, 2H, CH$_2$—CO$_2$H), 2.35 (s, 3H, 2—CH$_3$), 2.45 (s, 3H, 7—CH$_3$), 3.17 (t, 1H, C≡CH, J=2 Hz), 4.28 (broad s, 2H, CH$_2$C≡CH), 4.35 (m, 1H, NHCH), 4.67 (s, 2H, CH$_2$N), 6.82 (d, 2H, aromatic, J=9 Hz), 7.45 (s, 1H, 8—H), 7.75 (s, 1H, 5—H), 7.77 (d, 2H, aromatic, J=9 Hz), 8.23 (d, 1H, NH, J=8 Hz);

Mass Spectrum: (positive ion FAB) m/e 491 (P+1);
Elemental Analysis Found C, 60.1; H, 5.4; N, 10.6;
C$_{26}$H$_{26}$N$_4$O$_6$.1.5H$_2$O requires C, 60.3; H, 5.6; N, 10.8%

The quinazolinone used as starting material was obtained as follows:

A mixture of 3,4-dimethylacetanilide (16.3 g), ethyl carbamate (14 g), phosphorus pentoxide (30 g) and xylene (55 ml) was stirred vigorously using a mechanical stirrer under an atmosphere of argon. The mixture was slowly heated to approximately 60° C. whereupon a visible reaction ensued with the evolution of heat and with an increase in the viscosity of the mixture. The temperature of the mixture was raised over a period of 90 minutes to 150° C. and the mixture was stirred at this temperature for 2 hours during which time more phosphorus pentoxide (12 g in total) was added portionwise. The mixture was cooled and the xylene was decanted. A mixture of ice and water (250 ml) was added to the residue and the mixture was stirred for 30 minutes and filtered. The solid was analysed by thin layer chromatography using ethyl acetate as solvent and if it contained any product it was purified by chromatography as described for the residue obtained below. The filtrate was cooled in an ice bath to a temperature of less than 5° C. and the acidity of the solution was reduced to pH 5 by the addition of a concentrated aqueous sodium hydroxide solution. The mixture was extracted with ethyl acetate (2×50 ml) and the combined extracts were dried over magnesium sulphate, filtered and evaporated. The residue was purified by chromatography on a silica gel column using a 1:1 v/v mixture of methylene chloride and ethyl acetate as eluent. There were thus obtained, in order of elution, 3,4-dihydro-2,6,7-trimethylquinazolin-4-one (2 g) and 3,4-dihydro-2,5,6-trimethylquinazolin-4-one (2 g).

A mixture of the former compound (0.94 g), N-bromosuccinimide (0.9 g), benzoyl peroxide (10 mg) and chloroform (35 ml) was heated to reflux for 28 hours. The mixture was cooled to laboratory temperature and filtered. The solid was washed with chloroform and with a warm solution of ethyl acetate. There was thus obtained 6-bromomethyl-3,4-dihydro-2,7-dimethylquinazolin-4 one (0.56 g), m.p. >340° C.

The process described in Example 1 was repeated except that diethyl N-[2-fluoro-4-(prop-2-ynyl)aminobenzoyl]-L-glutamate (prepared as described in UK Patent Specification No. 2188319A) was used in place of diethyl N-[p-(prop-2-ynyl)aminobenzoyl]-L-glutamate. There was thus obtained N-[4--[N-(3-,4-dihydro-2,7-dimethyl-4-oxoquinazolin-6- yl-methyl)-N-(prop-2-ynyl)amino]-2-fluorobenzoyl]-L-glutamic acid (containing one equivalent of water ), m.p. 240°–245° C.

EXAMPLE 2

The process described in Example 1 was repeated using the appropriate 6-bromomethylquinazolinone in place of 6-bromomethyl-3,4-dihydro-2,7-dimethylquinazolin-4-one and the appropriate diethyl L-glutamate as starting materials. There were thus obtained the compounds described in the following table, the structures of which were confirmed by proton magnetic resonance and mass spectroscopy and by elemental analysis.

The appropriate 6-bromomethylquinazolinone was prepared using the process described in Example 1 concerning the preparation of starting materials except that the appropriate acetanilide was used in place of 3,4-dimethylacetanilide.

TABLE I

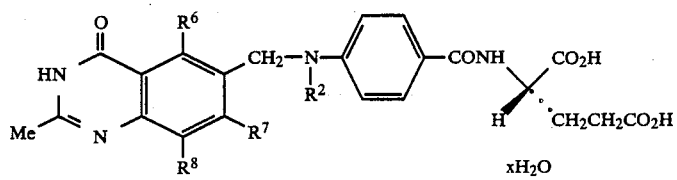

xH₂O

| Example 2 (Note) | R² | R⁶ | R⁷ | R⁸ | x | m.p. |
|---|---|---|---|---|---|---|
| | prop-2-ynyl | H | fluoro | H | 0.8 | 140–150° C. (dec.) |
| | prop-2-ynyl | H | chloro | H | 1.0 | 205–207° C. (dec.) |
| (1) | prop-2-ynyl | H | H | chloro | 0.8 | 215–219° C. (dec.) |
| | prop-2-ynyl | H | H | methoxy | 1.0 | 168–190° C. (dec.) |
| | prop-2-ynyl | chloro | H | H | 0.5 | 163–185° C. (dec.) |
| (2) | methyl | H | methyl | H | 2.0 | 208° C. (dec.) |
| (3) | H | H | methyl | H | 0.8 | 182–184° C. |
| (4) | 2-fluoroethyl | H | methyl | H | 1.3 | 185–190° C. |

Note (1): 2-Chloro-4-methylacetanilide (18 g) was used as the starting material and only one isomer, 8-chloro-2,6-dimethyl-quinazolin-4-one (0.6 g), was obtained from the first part of the process described in Example 1 concerning the preparation of starting materials. In the second part of that process the mixture of the quinazolinone, N-bromosuccinimide, benzoyl peroxide and chloroform was heated to reflux for 66 hours.

Note (2): Diethyl N-[p-methylaminobenzoyl]-L-glutamate (Journal of Heterocyclic Chemistry, 1975, 12, 1283) was used.

Note (3): Diethyl N-[p-aminobenzoyl]-L-glutamate was obtained as described in UK Patent Specification No. 2188319A.

Note (4): Diethyl N-[p.-(2-fluoroethyl)aminobenzoyl]-L-glutamate was obtained as described in UK Patent Specification No. 218B319A.

EXAMPLE 3

The process described in Example 1 was repeated using 6-(1-bromoethyl)-3,4-dihydro-2-methylquinazolin-4-one as starting material in place of 6-bromomethyl-3,4-dihydro-2,7-dimethylquinazolin-4-one. There was thus obtained N-[p-N-[1-(3,4-dihydro-2-methyl-4- oxoquinazolin-6-yl)ethyl]-N-(prop-2-ynyl)amino]benzoyl]-L-glutamic acid as a monohydrate, m.p. 157° C.

The quinazoline used as starting material was obtained using the process described in Example 1 concerning the preparation of starting materials except that p-ethylacetanilide was used in place of 3,4-dimethylacetanilide. Only one isomer, 6-ethyl-2-methylquinazolin-4-one, is obtained from the first part of that process.

The process described in Example 1 was repeated except that 6-(1-bromoethyl)-3,4-dihydro-2-methyl-quinazolin-4-one and diethyl N-[p-methylaminobenzoyl]-L-glutamate were used as starting materials. There was thus obtained N-[p-[N-[1-(3,4-dihydro-2-methyl-4-oxoquinazolin-6-yl)ethyl]-N-methylamino]-benzoyl]-L-glutamic acid (containing 1.5 equivalents of water), m.p. 165°-185°C.

EXAMPLE 4

The process described in Example 1 was repeated using the appropriate 6-bromomethylquinazolin-4-one and the appropriate diethyl L-glutamate as starting materials. Unless it is otherwise stated the appropriate L-glutamate was obtained as described in UK Patent Specification No. 2188319A. There were thus obtained the compounds described in the following table, the structures of which were confirmed by proton magnetic resonance and mass spectroscopy and by elemental analysis.

TABLE II

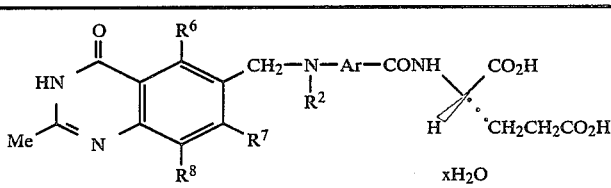

xH$_2$O

| Example 4 (Note) | R$^2$ | R$^6$ | R$^7$ | R$^8$ | Ar | x | m.p. (°C.) |
|---|---|---|---|---|---|---|---|
|  | ethyl | H | methyl | H | thien-2,5-diyl | 1.8 | 182–188 |
|  | methyl | H | methyl | H | thien-2,5-diyl | 0.8 | 191–193 |
| (1) | methyl | H | methyl | H | pyrid-2,5-diyl | 0.5 | 228–230 |

Note (1): The —CONH— group is in the 2-position of the pyridine ring.

EXAMPLE 5

A mixture of 6-bromomethyl-3,4-dihydro-2,8-dimethyl-3-pivaloyloxymethylquinazolin-4-one (0.63 g), diethyl N-[p-(prop-2-ynyl)aminobenzoyl]-L-glutamate (0.62 g), 2,6-lutidine (0.6 ml) and dimethylformamide (6 ml) was stirred at 80° C. under an atmosphere of argon for 19 hours. The mixture was cooled to laboratory temperature, a mixture of ice and water (10 ml) was added and the resultant mixture was stirred for 2 hours and filtered. The solid obtained was dried and purified by chromatography on a silica gel column using ethyl acetate as eluent.

A mixture of the product obtained (0.56 g), ethanol (4.0 ml) and aqueous N-sodium hydroxide solution (3.4 ml) was stirred at laboratory temperature for 5 hours. The mixture was evaporated to dryness, the residue was dissolved in de-ionised water and the solution was acidified to pH 2.5 by addition of aqueous 2N-hydrochloric acid solution. The mixture was centrifuged and the solid residue was washed with water (5×20 ml) and dried. The was thus obtained N-[p-[N-(3,4-dihydro-2,8-dimethyl-4-oxoquinazolin-6-ylmethyl)-N-(-prop-2=ynyl)amino]benzoyl]-L-glutamic acid (containing 2 equivalents of water; 0.13 g), m.p. 165°-173°.

NMR Spectrum: (CD$_3$SOCD$_3$) 2.0 (m, 2H, CH$_2$), 2.32 (broad t, 2H, CH$_2$CO$_2$H), 2.32 (s, 3H, 2—CH$_3$), 2.5 (s, 3H, 8—CH$_3$), 3.18 (t, 1H, C≡CH, J=2 Hz), 4.32 (m, 3H, CH$_2$C≡CH and NHCH), 4.72 (s, 2H, CH$_2$N), 6.85 (d, 2H, aromatic, J=8Hz), 7.56 (d, 1H, 7—H), 7.75 (d, 2H, aromatic, J=8 Hz), 7.82 (d, 1H, 5—H), 8.2 (broad d, 1H, NH);

Mass Spectrum: (positive ion FAB) m/e 491 (P+1); Elemental Analysis: Found C, 58.8; H, 5.2; N, 10,6; C$_{26}$H$_{26}$N$_4$O$_6$.2H$_2$O requires C, 59.3; H, 5.7; N, 10.6%.

The quinazolinone used as starting material was obtained using the first part of the process described in Example 1 concerning the preparation of starting materials except that 2,4-dimethylacetanilide was used in place of 3,4-dimethylacetanilide. Only one isomer, 3,4-dihydro-2,6,8-trimethylquinazolin-4-one, was obtained. Sodium hydride (2.39 g) was added to a stirred suspension of the product thus obtained (9.3 g) in dimethylformamide (100 ml) and the mixture was stirred at laboratory temperature for 1 hour. A solution of chloromethyl pivalate (8.23 ml) in dimethylformamide (20 ml) was added and the mixture was stirred at laboratory temperature for 18 hours, then poured onto a mixture of ice water (350 ml). The precipitate was filtered off, dried and purified by chromatography on a silica gel column using methylene chloride as eluent. There was thus obtained 3,4-dihydro-2,6,8-trimethyl-3-pivaloyloxymethylquinazolin-4-one (8.7 g).

A mixture of the product so obtained (7.8 g), N-bromosuccinimide (4.6 g) and carbon tetrachloride (200 ml) was irradiated with a 275 watt sun-lamp for 5 hours then stored at 4° C. for 17 hours. The precipitate was filtered off, dried and purified by chromatography on a silica gel column using ethyl acetate and petroleum ether (b.p. 60°-80° C., 1:4 v/v) as eluent. There were thus obtained 6-bromomethyl-3,4-dihydro-2,8-dimethyl-3-pivaloyloxymethyl-quinazolin-4-one (0.67 g) and 6,8-di(bromomethyl)-3,4-dihydro-3-pivaloyloxymethyl-quinazoline-4-one (0.36 g).

EXAMPLE 6

The process described in Example 5 was repeated using the appropriate 6-bromomethylquinazolinone in place of 6-bromomethyl-3,4-dihydro-2,8-dimethyl-3-pivaloyloxymethylquinazolin-4-one and the appropriate diethyl L-glutamate as starting materials. Unless it is otherwise stated the appropriate diethyl L-gluamate was obtained as described in UK Patent Specification No. 2188319A. There were thus obtained the compounds described in the following table, the structures of which were confirmed by proton magnetic resonance and mass spectroscopy and by elemental analysis. The appropriate 6-bromomethylquinazolinone was prepared using the process described in Example 5 concerning the preparation of starting materials except that the appropriate acetanilide was used in place of 2,4-dimethylacetanilide.

TABLE III

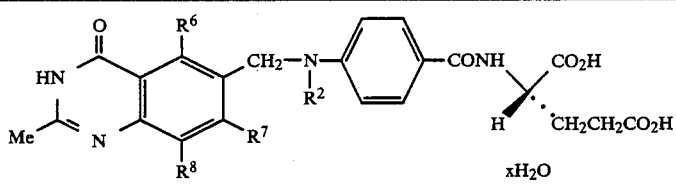

| Example 6 (Note) | R² | R⁶ | R⁷ | R⁸ | x | m.p. |
|---|---|---|---|---|---|---|
| (1) | prop-2-ynyl | H | methoxy | H | 1 | 184–188° C. |
| (1) | ethyl | H | methoxy | H | 2.5 | 164–168° C. |

Note (1): 3-Methoxy-4-methylacetanilide (25.1 g) was used in place of 3,4-dimethylacetanilide as the starting material in the first part of the process described in Example 1 concerning the preparation of starting materials to give 2,6-dimethyl-7-methoxyquinazolin-4-one (18.6 g).

EXAMPLE 7

A mixture of 6-bromomethyl-3,4-dihydro-2,7-dimethylquinazolin-4-one (0.27 g), diethyl N-[5-methylaminothiazole-2-carbonyl]-L-glutamate (0.56 g), calcium carbonate (0.2 g) and dimethylformamide (4 ml) was stirred at 95° C. for 2.5 hours under an atmosphere of argon. The mixture was cooled and filtered and the filtrate was evaporated to dryness. The residue was purified by chromatography on a silica gel column using initally methylene chloride as eluent and then increasing the polarity of the solvent stepwise till a 25:2 v/v mixture of methylene chloride and ethanol was used as eluent.

A mixture of the product so obtained (0.37 g), ethanol (8 ml), water (8 ml) and aqueous N-sodium hydroxide solution (4.2 ml) was stirred at laboratory temperature under an atmosphere of argon for 8 hours. The mixture was evaporated to a volume of approximately 5 ml and filtered into a centrifuge tube. The filtrate was acidified to pH 3 with 2N-hydrochloric acid. The resulting precipitate was isolated by centrifigation, washed four times with water and dried. There was thus obtained N-[5-[N (3,4-dihydro-2,7-dimethyl-4-oxoquinazolin-6-ylmethyl)-N-methylamino]thiazole-2-carbonyl]-L-glutamic acid (containing 1.25 equivalents of water; 0.23 g), m.p. 185°–190° C.

NMR Spectrum: ($CD_3SOCD_3$) 2.02 (m, 2H, $CH_2$), 2.30 (broad t, 2H, $CH_2CO_2H$), 2.32 (s, 3H, 2—$CH_3$), 2.39 (s, 3H, 7—$CH_3$), 3.06 (s, 3H, $NCH_3$), 4.36 (m, 1H, NHCH), 4.63 (broad d, 2H, $CH_2N$). 7.06 (s, 1H, thiazole-H), 7.45 (s, 1H, 8—H), 7.75 (s, 1H, 5—H), 8.34 (d, 1H, NH, J=8 Hz);

Mass Spectrum: (negative ion FAB) m/e (P-1) 472;
Elemental Analysis: Found C, 50,9; H, 4.8; N, 13.9;
$C_{21}H_{23}N_5O_6S.1.3H_2O$ requires C, 50.9; H, 5.1; N, 14.1%

The diethyl N-[5-methylaminothiazole-2-carbonyl]-L-glutamate used as starting material was obtained as follows:

Oxalyl chloride (13 ml) was added dropwise to a stirred suspension of 5-nitrothiazole-2-carboxylic acid (12.9 g; Chem. Ber. 1973, 106, 722) in a mixture of methylene chloride (80 ml and dimethylformamide (20 ml). The mixture was stirred at laboratory temperature for 30 minutes and evaporated to dryness to give 5-nitrothiazole-2-carbonyl chloride.

The product so obtained was dissolved in methylene chloride (150 ml) and added to a mixture of diethyl L-glutamate hydrochloride (35.4 g), triethylamine (51.2 g) and methylene chloride (250 ml) which was cooled in a bath of ice and water; the rate of addition being such that the temperature of the reaction mixture was maintained below 15° C. The mixture was allowed to warm to room temperature and stirred for 16 hours. The mixture was washed with water (2×300 ml), dried over magnesium sulphate, filtered and evaporated to dryness. The residue was purified by chromatography on a silica gel column using initially methylene chloride as eluent and then increasing the polarity of the solvent stepwise till a 19:1 v/v mixture of methylene chloride and ethyl acetate was used as eluent. There was thus obtained diethyl N-5-nitrothiazole-2-carbonyl]-L-glutamate as a gum (24.3 g).

A mixture of the product so obtained (4 g), iron powder (10 g) and glacial acetic acid (44 ml) was stirred vigorously at 80° C. for 30 minutes. The mixture was cooled to laboratory temperature, poured into water (100 ml) and extracted with methylene chloride (2×200 ml). The combined organic extracts were washed with water (1×100 ml). dried over magnesium sulphate, filtered and evaporatated to dryness to give diethyl-N-[5-aminothiazole-2-carbonyl]-L-glutamate as gum (3.6 g).

A mixture of the product so obtained (3.6 g), methyl iodide (2 ml) and dimethylformamide (10 ml) was stirred at 60° C. under an atmosphere of argon for 1 hour. A second portion of methyl iodide (1 ml) was added and the mixture was stirred at 60° C. for a further 1 hour. The mixture was cooled, poured into a saturated aqueous sodium bicarbonate solution (50 ml) and extracted with ethyl acetate (3×30 ml). The combined extracts were washed with water, dried over magnesium sulphate, filtered and evaporated to dryness. The residue was purified by chromatography on a silica gel column using initally methylene chloride as eluent and then increasing the polarity of the solvent stepwise till a 10:1 v/v mixture of methylene chloride and ethyl acetate was used as eluent. There were thus obtained diethyl N-[5-dimethylaminothiazole-2-carbonyl]-L-glutamate (0.84 g) and diethyl N-[5-methylaminothiazole-2-carbonyl]-L-glutamata (1.1 g).

EXAMPLE 8

The process described in Example 1 was repeated except that ethyl N-[p-(prop-2-ynyl)aminobenzoyl]-L-valinate was used in place of diethyl N-[p-(prop-2-ynyl)aminobenzoyl-L-glutamate. The was thus obtained N-[p-[N-(3,4-dihydro-2,7-dimethyl-4-oxoquinazolin-6-ylmethyl)-N-(prop-2-ynyl)amino]benzoyl]-L-valine (containing one equivalent of water), m.p. 250°–255° C.

NMR Spectrum: (CD$_3$SOCD$_3$) 0.95 (d of d's, 6H, 2×CH$_3$), 2.17 (m, 1H, CH), 2.31 (s, 3H, 2—CH$_3$), 2.45 (s, 3H, 7—CH$_3$), 3.18 (broad t, 1H, C≡CH), 4.25 (broad t, 3H, CH$_2$C≡CH and NHCH), 4.68 (s, 2H, CH$_2$N), 6.82 (d, aromatic, J=9 Hz), 7.42 (s, 1H, 8—H), 7.73 (s, 1H, 5—H), 7.76 (d, 2H, aromatic, J=9 Hz), 7.98 (d, 1H, NH, J=8Hz):

Mass Spectrum: (negative ion FAB) m/e (P-1) 459;
Elemental Analysis: Found C, 65.2 H, 6.1; N, 11.8; C$_{26}$H$_{28}$N$_4$O$_4$.1H$_2$O requires C, 65.3; H, 6.3; N, 11.7%.

The ethyl N-[p-(prop-2-ynyl)aminobenzoyl]-L-valinate used as a starting material was prepared from ethyl valinate hydrochloride in an analogous manner to the preparation of diethyl N-[p-(prop-2-ynyl)aminobenzoyl]-L-glutamate from diethyl glutamate hydrochloride as described in *J. Med. Chem.*, 1986, 29, 1114.

EXAMPLE 9

The process described in Example 8 was repeated except that methyl N-[2-fluoro-4-(prop-2-ynyl)aminobenzoyl]-L-valinate was used in place of ethyl N-[p-(prop-2-ynyl)aminobenzoyl]-L-valinate. There were thus obtained in turn methyl N-[4-[N-(3,4-dihydro-2,7-dimethyl-4-oxoquinalozolin-6-ylmethyl)-N-(prop-2-ynyl)amino]-2-fluorobenzoyl]-L-valinate, m.p. 237°-240° C. and, after the second step of the process, N-4-[N-(3,4-dihydro-2,7-dimethyl-4-oxoquinazolin-6-ylmethyl)-N-(prop2-ynyl)amino]-2-fluorobenzoyl]-L-valine (containing 0.5 equivalents of water ), m.p. 255°-257° C. (decomp.).

The methyl N-[2-fluoro-4-(prop-2-ynyl)aminobenzoyl]-L-valinate used as a starting material was prepared from methyl valinate hydrochloride in an analogous manner to the preparation of diethyl N-[2-fluoro-4-(prop-2-ynyl)aminobenzoyl]-L-glutamate from diethyl glutamate hydrochloride as described in UK Patent Specifications Nos. 2175903 and 2188319A.

EXAMPLE 10

Diphenylphosphoryl azide (0.±1 g) and triethylamine (0.55 ml) were added successively to a mixture of p-[N-(3,4-dihydro-2,7-dimethyl-4-oxoquinazolin-6-ylmethyl)-N-(prop-2-ynyl)amino]benzoic acid (as its trifluoroacetic acid salt; 0.46 g) and dimethylformamide (20 ml) and the mixture was stirred at laboratory temperature for 18 hours. The mixture was filtered. 1,8-Diazabicyclo[5,4,0]undec-7-ene (0.6 ml) was added to a mixture of the solid so obtained, L-tert-leucine (0.26 g) and dimethylformamide (20 ml) and the mixture was stirred at laboratory temperature for 18 hours. The mixture was evaporated to a volume of approximately 5 ml, poured into a mixture of ice water (50 ml), acidified to pH 3 with aqueous 0.2 N-hydrochloric acid solution and centrifuged. The solid residue was washed with water (5 x 20 ml) and dried. The was thus obtained N-[p-[N-(3,4-dihydro-2,7-dimethyl-4-oxoquinazolin-6-ylmethyl)-N-(prop-2ynyl)amino]benzoyl]-L-tert-leucine (containing 1.5 equivalents of water, 0.33 g), m.p. 233°-236° C.

NMR Spectrum: (CD$_3$SOCD$_3$) 1.02 (s, 9H 3×CH$_3$) 2.30 (s . 2—CH$_3$), 2.46 (s, 3H, 7—CH$_3$), 3.17 (s, 1H, C≡CH), 4.28 (s, 2H, CH$_2$C≡CH), 4.33 (d, 1H, NHCH, J=9 Hz), 4.68 (s, 2H, CH$_2$N), 6.78 (d, 2H, aromatic, J=9 Hz), 7.42 (s, 1H, 8—H), 7.68 (d, 1H, NH, J=9 Hz), 7.73 (s, 1H, 5—H), 7.75 (d, 2H, aromatic, J=9 Hz);

Mass Spectrum: (positive ion FAB) m/e (P+1) 475;
Elemental Analysis: Found C, 64.4; H, 6.3; N, 11.0; C$_{27}$H$_{30}$N$_4$O$_4$.1.5H$_2$O requires C, 64.6; H, 6.6; N, 11.2%.

The p-[N-(3,4-dihydro-2,7-dimethyl-4-oxoquinazolin-6-ylmethyl)-N-(prop-2-ynyl)amino]benzoic acid (as its trifluoroacetic acid salt) used as a starting material, was obtained using the first part of the process described in Example 1, except that tert-butyl p-(prop-2-ynyl)aminobenzoate (obtained as described in UK Patent Specification No. 2188319A) was used in place of diethyl N-[p-(prop-2-ynyl)aminobenzoyl]-L-glutamate, followed by a mixture of the product so obtained (2.8 g) and trifluoroacetic acid (20 ml) being stirred together at laboratory temperature for 15 minutes and evaporated to dryness.

EXAMPLE 11

The process described in Example 10 was repeated using L-phenylglycine (i.e. (S)-α-aminophenylacetic acid) in place of L-tert-leucine. There was thus obtained N-[p-]N-(3,4-dihydro-2,7-dimethyl-4-oxoquinazolin-6-ylmethyl)-N-(prop-2-ynyl)amino]benzoyl]-L-phenylglycine, (containing 0.75 equivalents of water) m.p. 199°-201° C.

What is claimed is:

1. A quinazoline of the formula:

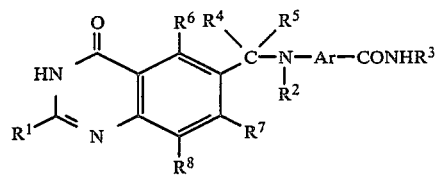

wherein
R$^1$ is alkyl, cycloalkyl, alkenyl, alkynyl, alkoxy or alkylthio each of up to 6 carbon atoms;
or R$^1$ is aryl, aryloxy, arylthio or arylalkyl each of up to 10 carbon atoms;
or R$^1$ is halogeno, hydroxy or mercapto,
or R$^1$ is alkyl of up to 3 carbon atoms which bears one or more substituents selected from halogeno, hydroxy, amino, alkoxy, alkanoyloxy, alkylthio, alkylamino, dialkylamino and alkanoylamino each of up to 6 carbon atoms and arylthio, aroyloxy and aroylamino each of up to 10 carbon atoms;
or R$^1$ is alkoxy of up to 3 carbon atoms which bears one or more substituents selected from hydroxy and alkoxy of up to 6 carbon atoms;
wherein R$^2$ is hydrogen, alkyl, alkenyl, alkynyl, hydroxyalkyl, alkoxyalkyl, mercaptoalkyl, alkylthioalkyl, halogenalkyl, cyanoalkyl, aminoalkyl, alkylaminoalkyl, dialkylaminoalkyl, alkanoylalkyl, carboxyalkyl, carbamoylalkyl or alkanoyl each of up to 6 carbon atoms or aroylalkyl of up to 10 carbon atoms;
wherein Ar is phenylene, naphthylene, thienylene, pyridylene, pyrimidinylene, thiazolylene or oxazolylene which is unsubstituted or which bears one or more substituents selected from halogeno, phenyl cyano, nitro, hydroxy, amino and carbamoyl and alkyl, alkoxy, halogenoalkyl, alkanoylamino, alkylthio and alkoxycarbonyl each of up to 6 carbon atoms;
wherein R$^1$ is such that —NHR$^3$ is the radical formed at the alpha-amino group of an amino acid selected from the class consisting of L-aspartic acid, L- glutamic acid, L-alanine, L-phenylalanine, L-serine, glycine, L-ornithine, L-valine, L-leucine, L-isoleucine, L-2-aminobutyric acid, L-norvaline, L-alloisoleucine, L-2-phenylglycine, L-tert-leucine and a poly-L-glutamic acid of the formula:

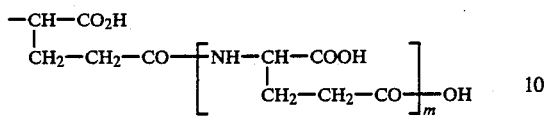

wherein m is an integer from 1 to 10;
wherein $R^4$ is hydrogen or alkyl, of up to 4 carbon atoms;
wherein $R^5$ is hydrogen or alkyl, of up to 4 carbon atoms; and
wherein each of $R^6$, $R^7$ and $R^8$ is hydrogen, hydroxy, alkyl, alkoxy, alkylthio, alkylamino or dialkylamino each of up to 4 carbon atoms;
or is phenyl, halogeno, nitro, cyano or amino; or is alkyl, alkoxy or alkylthio each of up to 4 carbon atoms which bears one or more substituents selected from halogeno, hydroxy, amino, alkoxy, alkylamino and dialkylamino each of up to 4 carbon atoms; provided that at least one of $R^4$, $R^5$, $R^6$, $R^7$ and $R^8$ is other than hydrogen;
or a pharmaceutically-acceptable salt or ester thereof.

2. A quinazoline as claimed in claim 1, wherein $R^1$ is methyl, ethyl, isopropyl, cyclopropyl, prop-2-enyl, prop-2-ynyl, methoxy, ethoxy, methylthio, phenyl, tolyl, phenoxy, benzyl, phenethyl, chloro, bromo, hydroxy, mercapto, fluoromethyl, difluoromethyl, trifluoromethyl, 2-fluoroethyl, chloromethyl, hydroxymethyl, 2-hydroxyethyl, aminomethyl, methoxymethyl, acetoxymethyl, methylthiomethyl, methylaminomethyl, dimethylaminomethyl, acetamidomethyl, 2-hydroxyethoxy, 2-methoxyethoxy or 2-ethoxyethoxy; wherein $R^2$ is hydrogen, methyl, ethyl, propyl, prop-2-enyl, but-2-enyl, prop-2-ynyl, but-2-ynyl, 2-hydroxyethyl, 3-hydroxypropyl, 2-methoxypropyl, 2-mercaptoethyl, 2methylthioethyl, 2-fluoroethyl, 2-chloroethyl, 2-bromoethyl, 3-fluoropropyl, cyanomethyl 2-cyanoethyl, 2aminoethyl, 2-methylaminoethyl, 2-dimethylaminoethyl, acetonyl, carboxymethyl, carbamoylmethyl or acetyl;
wherein Ar is 1,4-phenylene, thienylene, pyridylene, pyrimidinylene, thiazolylene or oxazolylene which is unsubstituted or which bears one or two substituents selected from fluoro, chloro, bromo, phenyl, cyano, nitro, hydroxy, amino, carbamoyl, methyl, ethyl, methoxy, ethoxy, fluoromethyl, difluoromethyl, trifluoromethyl and acetamido;
wherein $R^3$ is such that —$NHR^3$ is the radical formed at the alpha-amino group of L-glutamic acid, glycine, L-alanine, L-phenylalanine, L-serine, L-ornithine, L-aspartic acid, L-valine, L-leucine, L-isoleucine, L-2-aminobutyric acid, L-norvaline, L-alloisoleucine, L-2-phenylglycine, L-tert-leucine;
wherein $R^4$ is hydrogen methyl or ethyl
wherein $R^5$ is hydrogen, methyl or ethyl and
wherein each of $R^6$, $R^7$ and $R^8$ is hydrogen, hydroxy, methyl, ethyl, methoxy, ethoxy, methylthio, methylamino, dimethylamino, phenyl, fluoro, chloro, bromo, nitro, cyano, amino, fluoromethyl, difluoromethyl, trifluoromethyl, 2-fluoroethyl, hydroxymethyl or 2-hydroxyethyl;
provided that at least one of $R^4$, $R^5$, $R^6$, $R^7$ and $R^8$ is other than hydrogen;
or a pharmaceutically-acceptable salt or ester thereof.

3. A quinazoline as claimed in claim 1, wherein $R^1$ is methyl, ethyl, methoxy, fluoromethyl or hydroxymethyl;
wherein $R^2$ is hydrogen, methyl, ethyl, prop-2-enyl, prop-2-ynyl, 2-hydroxyethyl, 3-hydroxypropyl, 2-fluoroethyl, 2-bromoethyl, cyanomethyl, or acetonyl;
wherein Ar is 1,4-phenylene, thien-2,5diyl, pyrid-2,5-diyl or thiazol-2,5diyl which is unsubstituted or which bears one or two substituents selected from fluoro, chloro, hydroxy, amino, and methyl;
wherein $R^3$ is such that —$NHR^3$ is the radical formed at the alpha-amino group of L-glutamic acid, L-valine, L-leucine, L-isoleucine, L-2-aminobutyric acid, L-norvaline, L-alloisoleucine, L-2-phenylglycine, L-tert-leucine;
wherein $R^4$ is hydrogen or methyl;
wherein $R^5$ is hydrogen;
wherein $R^6$ is hydrogen, methyl, methoxy, fluoro or chloro;
wherein $R^7$ is hydrogen, methyl, methoxy, fluoro or chloro and
wherein $R^8$ is hydrogen, methyl, methoxy, fluoro or chloro; provided that at least one of $R^4$, $R^5$, $R^6$, and $R^7$ and $R^8$ is other than hydrogen.

4. A quinazoline as claimed in claim 1, wherein $R^1$ is methyl, ethyl, methoxy, fluoromethyl or hydroxymethyl;
wherein $R^2$ is hydrogen, methyl, ethyl, prop-2-enyl, prop-2-ynyl, 2-hydroxyethyl, 3-hydroxypropyl, 2-fluoroethyl or acetonyl;
wherein Ar is 1,4-phenylene, thien-2,5-diyl, pyrid-2,5-diyl or 2-fluoro-1,4-phenylene;
wherein $R^3$ is such that —$NHR^3$ is the radical of L-glutamic acid;
wherein $R^4$ is hydrogen or methyl;
wherein $R^5$ is hydrogen;
wherein $R^6$ is hydrogen or chloro;
wherein $R^7$ is hydrogen, methyl, fluoro or chloro and
wherein $R^8$ is hydrogen, methoxy or chloro; provided that at least one of $R^4$, $R^6$, $R^7$ and $R^8$ is other than hydrogen.

5. A quinazoline as claimed in claim 1, wherein $R^1$ is methyl;
wherein $R^2$ is hydrogen, methyl, ethyl, prop-2-ynyl or 2-fluoroethyl:
wherein Ar is 1,4-phenylene or thien-2,5-diyl; or is pyrid-2,5-diyl or thiazol-2,5-diyl each with the group —$CONHR^3$ in the 2-position; or is 2-fluoro-1,4-phenylene with the group —$CONHR^3$ in the 1-position;
wherein $R^3$ is such that —$NHR^3$ is the radical of L-glutamic acid, L-valine, L-2-phenylglycine or L-tert-leucine;
wherein $R^4$ is hydrogen or methyl;
wherein $R^5$ is hydrogen;
wherein $R^6$ is hydrogen or chloro;
wherein $R^7$ is hydrogen, methyl, methoxy, fluoro or chloro and
wherein $R^8$ is hydrogen, methyl, methoxy or chloro; provided that at least one of $R^4$, $R^6$, $R^7$ and $R^8$ is other than hydrogen.

6. A compound selected from the group consisting of:

N-[p-[N-(3,4-dihydro-2,7-dimethyl-4-oxoquinazolin-6-ylmethyl)-N-(prop-2-ynyl)amino]benzoyl]-L-glutamic acid, N-[p-[N-(3,4-dihydro-2,7-dimethyl-4-oxoquinazolin-6-ylmethyl-N-methylamino]benzoyl]-L-glutamic acid, N-[p-[N-(7-fluoro-3,4-dihydro-2-methyl-4-oxoquinazolin-6-ylmethyl)-N-(prop-2-ynyl)amino]benzoyl]-L-glutamic acid, N-[p-[N-(7-chloro-3,4-dihydro-2-methyl-4-oxoquinazolin-6-ylmethyl)-N-(prop-2-ynyl)amino]benzoyl]-L-glutamic acid, N-[p-[N-(3,4-dihydro-8-methoxy-2-methyl-4-oxoquinazolin-6-ylmethyl)-N-(prop-2-ynyl)amino]benzoyl]-L-glutamic acid, N-[p-[N-[1-(3,4-dihydro-2-methyl-4-oxoquinazolin-6-yl)ethyl]-N-(prop-2-ynyl)amino]benzoyl]-L-glutamic acid and N-[p-[N-[1-(3,4-dihydro-2-methyl-4-oxoquinazolin-6-yl)ethyl]-N-methylamino]benzoyl]-L-glutamic acid.

7. A compound selected from the group consisting of:

N-[4-[N-(3,4-dihydro-2,7-dimethyl-4-oxoquinazolin-6-ylmethyl)-N-(prop-ynyl)amino]-2-fluorobenzoyl]-L-glutamic acid, N-[5-[N-(3,4-dihydro-2,7-dimethyl-4-oxoquinazolin-6-ylmethyl)-N-ethylamino]-2-thenoyl]-L-glutamic acid, N-[5-[N-(3,4-dihydro-2,7-dimethyl-4-oxoquinazolin-6-ylmethyl)-N-methylamino]picolinoyl]-L-glutamic acid, N-[5-[N-(3,4-dihydro-2,7-dimethyl-4-oxoquinazolin-6-ylmethyl)-N-methylamino]thiazole-2-carbonyl]-L-glutamic acid, N-[p-[N-(3,4-dihydro-2,7-dimethyl-4-oxoquinazolin-6-ylmethyl)-N-prop-2-ynyl)amino]benzonyl]-L-valine and N-[4-[N-(3,4-dihydro-2,7-dimethyl-4-oxoquinazolin-6-ylmethyl)-N-(prop-2-ynyl)amino]-2-fluorobenzoyl]-L-valine.

8. A pharmaceutical composition comprising a quinazoline as claimed in claim 1, or a pharmaceutically-acceptable salt or ester thereof, together with a pharmaceutically-acceptable diluent or carrier.

9. A method for producing an anti-tumour effect in a warm-blooded animal in need of such treatment, which comprises administering to said animal an effective amount of at least one quinazoline as claimed in claim 1.

* * * * *